US010857245B2

(12) United States Patent
Oka et al.

(10) Patent No.: US 10,857,245 B2
(45) Date of Patent: Dec. 8, 2020

(54) DIAGNOSTIC IMAGING AGENT FOR EARLY BONE METASTASIS FROM CANCER

(71) Applicant: NIHON MEDI-PHYSICS CO., LTD., Tokyo (JP)

(72) Inventors: Shuntaro Oka, Tokyo (JP); Masaru Kanagawa, Tokyo (JP); Akiharu Otaka, Tokyo (JP); Masako Teramachi, Tokyo (JP); Satoshi Watanabe, Tokyo (JP); Toshie Nagatomo, Tokyo (JP)

(73) Assignee: NIHON MEDI-PHYSICS CO., LTD., Tokyo (JP)

( * ) Notice: Subject to any disclaimer, the term of this patent is extended or adjusted under 35 U.S.C. 154(b) by 0 days.

(21) Appl. No.: 15/579,278

(22) PCT Filed: Jun. 1, 2016

(86) PCT No.: PCT/JP2016/002654
§ 371 (c)(1),
(2) Date: Dec. 4, 2017

(87) PCT Pub. No.: WO2016/194372
PCT Pub. Date: Dec. 8, 2016

(65) Prior Publication Data
US 2018/0161463 A1 Jun. 14, 2018

(30) Foreign Application Priority Data
Jun. 4, 2015 (JP) .................................. 2015-113587

(51) Int. Cl.
A61K 51/00 (2006.01)
A61M 36/14 (2006.01)
A61K 51/04 (2006.01)
A61K 49/04 (2006.01)

(52) U.S. Cl.
CPC ...... A61K 51/0406 (2013.01); A61K 49/0433 (2013.01)

(58) Field of Classification Search
None
See application file for complete search history.

(56) References Cited

U.S. PATENT DOCUMENTS

| | | | |
|---|---|---|---|
| 7,632,486 B1 | 12/2009 | Ogata et al. | |
| 9,381,259 B2* | 7/2016 | Ito | A61K 51/0406 |
| 9,387,266 B2* | 7/2016 | Ito | A61K 51/0406 |
| 2002/0131934 A1 | 9/2002 | Suzuki et al. | |
| 2010/0032575 A1* | 2/2010 | Iagaru | G01T 1/1611 250/362 |
| 2010/0092464 A1 | 4/2010 | Kavanaugh et al. | |
| 2012/0010601 A1* | 1/2012 | Simon | A61K 41/0085 606/1 |

FOREIGN PATENT DOCUMENTS

WO WO 2007/016285 A2 2/2007

OTHER PUBLICATIONS

Nanni et al. (Eur. J. Nucl. Med. Mol. Imaging 2013, 40 (Suppl 1), S11-S17.*
Nemeth et al. (J. Natl. Cancer Inst. 2002, 94, 17-25).*
Nye et al. (Nucl. Med. Biol. 2011, 38, 1035-1041).*
Schuster et al. (J. Nucl. Med. 2007, 48, 56-63).*
Schuster et al. (Radiol. 2011, 259, 852-861).*
Keller et al. (J. Cellular Biochem 2004, 91, 718-729).*
Schuster et al., Initial Experience with the Radiotracer Anti-1-Amino-3-[18]F-Fluorocyclobutane-1-Carboxylic Acid with PET/CT in Prostate Carcinoma, *The Journal of Nuclear Medicine*, Jan. 2007, pp. 56-63, vol. 48, No. 1, Society of Nuclear Medicine and Molecular Imaging, Reston, VA, U.S.A. http://jnm.snmjournals.org/content/48/1/56.
Schuster etal., Detection of Recurrent Prostate Carcinoma with anti-1-Amino-3-1[18]F-Fluorocyclobutane-1-Carboxylic Acid PET/CT and [111]In-Capromab Pendetide SPECT/CT, *Radiology*, Jun. 2011, pp. 852-861, vol. 259, No. 3, Radiological Society of North America. https://doi.org/10.1148/radiol.11102023.
Oka et al., Differences in Transport Mechanisms of trans-1-Amino-3-[$^{18}$F]Fluorocyclobutanecarboxylic Acid in Inflammation, Prostate Cancer, and Glioma Cells: Comparison with L-[Methyl-$^{11}$C]Methionine and 2-Deoxy-2-[$^{18}$F]Fluoro-D-Glucose, *Molecular Imaging and Biology*, Jun. 2014, pp. 322-329, vol. 16, Issue 3, Springer US. https://doi.org/10.1007/s11307-013-0693-0.
Inoue etal., Phase IIa Clinical Trial of Trans-1-Amino-3-[18]F-Fluoro-Cyclobutane Carboxylic Acid in Metastatic Prostate Cancer, *Asia Oceania Journal of Nuclear Medicine and Biology*, 2014 Autumn, pp. 87-94, vol. 2, No. 2. PMCID: PMC4937703.
Nakai et al., Pitfalls of FDG-PET for the diagnosis of osteoblastic bone metastases in patients with breast cancer, *European Journal of Nuclear Medicine and Molecular Imaging*, Nov. 2005, pp. 1253-1258, vol. 32, Issue 11, Springer-Verlag. https://doi.org/10.1007/s00259-005-1842-8.
Schuster et al., Anti-3-[$^{18}$F]FACBC Positron Emission Tomography—Computerized Tomography and [111]In-Capromab Pendetide Single Photon Emission Computerized Tomography—Computerized Tomography for Recurrent Prostate Carcinoma: Results of a Prospective Clinical Trial, *The Journal of Urology*, May 2014, pp. 1446-1453, vol. 191, Issue 5, Elsevier Inc. http://dx.doi.org/10.1016/j.juro.2013.10.065.
Schuster et al., Report of a clinical trial of anti-1 amino 3 [18F]fluorocyclobutane-1 -carboxylic acid (anti-[18F]FACBC) PET-CT in recurrent prostate carcinoma, *The Journal of Nuclear Medicine*, May 2010, p. 456, vol. 51, No. Supplement 2, Society of Nuclear Medicine and Molecular Imaging. ISSN: 2159-662X.
Tade et al., Preliminary findings of anti-[$^{18}$F] FACBC (FACBC) PET-CT imaging of breast cancer, *The Journal of Nuclear Medicine*, May 1, 2015, p. 567, vol. 56, No. Supplement 3, Society of Nuclear Medicine and Molecular Imaging. ISSN: 2159-662X.

(Continued)

*Primary Examiner* — Michael G. Hartley
*Assistant Examiner* — Melissa J Perreira
(74) *Attorney, Agent, or Firm* — Buchanan Ingersoll & Rooney PC

(57) ABSTRACT

There is provided a diagnostic imaging agent for early bone metastasis from cancer, containing trans-1-amino-[$^{18}$F]fluorocyclobutanecarboxylic acid or a pharmaceutically acceptable salt thereof as an active ingredient.

7 Claims, 8 Drawing Sheets

(56) References Cited

OTHER PUBLICATIONS

Suzuki et al., Diagnostic performance and safety of NMK36 (trans-1-amino-3-[$^{18}$F]fluorocyclobutanecarboxylic acid)-PET/CT in primary prostate cancer: multicenter Phase IIb clinical trial, *Japanese Journal of Clinical Oncology*, 2016, pp. 152-162, vol. 46, No. 2, Oxford. doi: 10.1093/jjco/hyv181.

Oka et al., Feasibility of Fluciclovine (FACBC) for bone metastasis diagnosis in prostate and breast cancer: Evaluation by using triple-tracer autoradiography with 14CFluciclovine/3H-FDG/99mTc-HMDP in rat osteolytic/osteoblastic bone metastasis models, *The Journal of Nuclear Medicine*, May 1, 2016, p. 1360, vol. 57, No. Supplement 2, Society of Nuclear Medicine and Molecular Imaging. ISSN: 2159-662X.

International Search Report (PCT/ISA/210) dated Aug. 30, 2016, by the Japan Patent Office as the International Searching Authority for International Application No. PCT/JP2016/002654.

Written Opinion (PCT/ISA/237) dated Aug. 30, 2016, by the Japan Patent Office as the International Searching Authority for International Application No. PCT/JP2016/002654.

Amzat et al.: "Unusual Presentations of Metastatic Prostate Carcinoma as Detected by anti-3 F-18 FACBC PET/CT," Clinical Nuclear Medicine, vol. 36, No. 9, Sep. 1, 2011, pp. 800-802.

Satoh et al.: "MP12-08 Phase IIa Clinical Trial of a New PET Tracer NMK36 in Metastatic Prostate Cancer," Journal of Urology, vol. 191, No. 4S, May 17, 2014, pp. e107-e108.

Extended Search Report issued by the European Patent Office in corresponding European Patent Application No. 16802812.4-1111 dated Dec. 6, 2018.

Office Action issued by the Taiwanese Patent Office in corresponding Taiwanese Patent Application No. 105117276 dated Dec. 5, 2019, which rejects claims 1-5 for lack of novelty based on D1 and D2 (3 pages).

Notice of Reasons for Refusal issued by the Japanese Patent Office in corresponding Japanese Patent Application No. 2017-563143 dated Apr. 7, 2020 (10 pages including partial English translation).

Office Action issued by the State Intellectual Property Office of People's Republic of China in corresponding Chinese Patent Application No. 201680032390.8 dated Apr. 26, 2020 (9 pages).

Examination report No. 1 for standard patent application, issued by the Australian Government in corresponding Australian Application No. 2016271942 dated Jul. 30, 2020 (5 pages).

Office Action dated Oct. 6, 2020, by the Brazilian Patent Office in corresponding Brazilian Patent Application No. 112017026003-4 and an English translation of the Office Action. (9 pages).

\* cited by examiner

[Fig. 1]
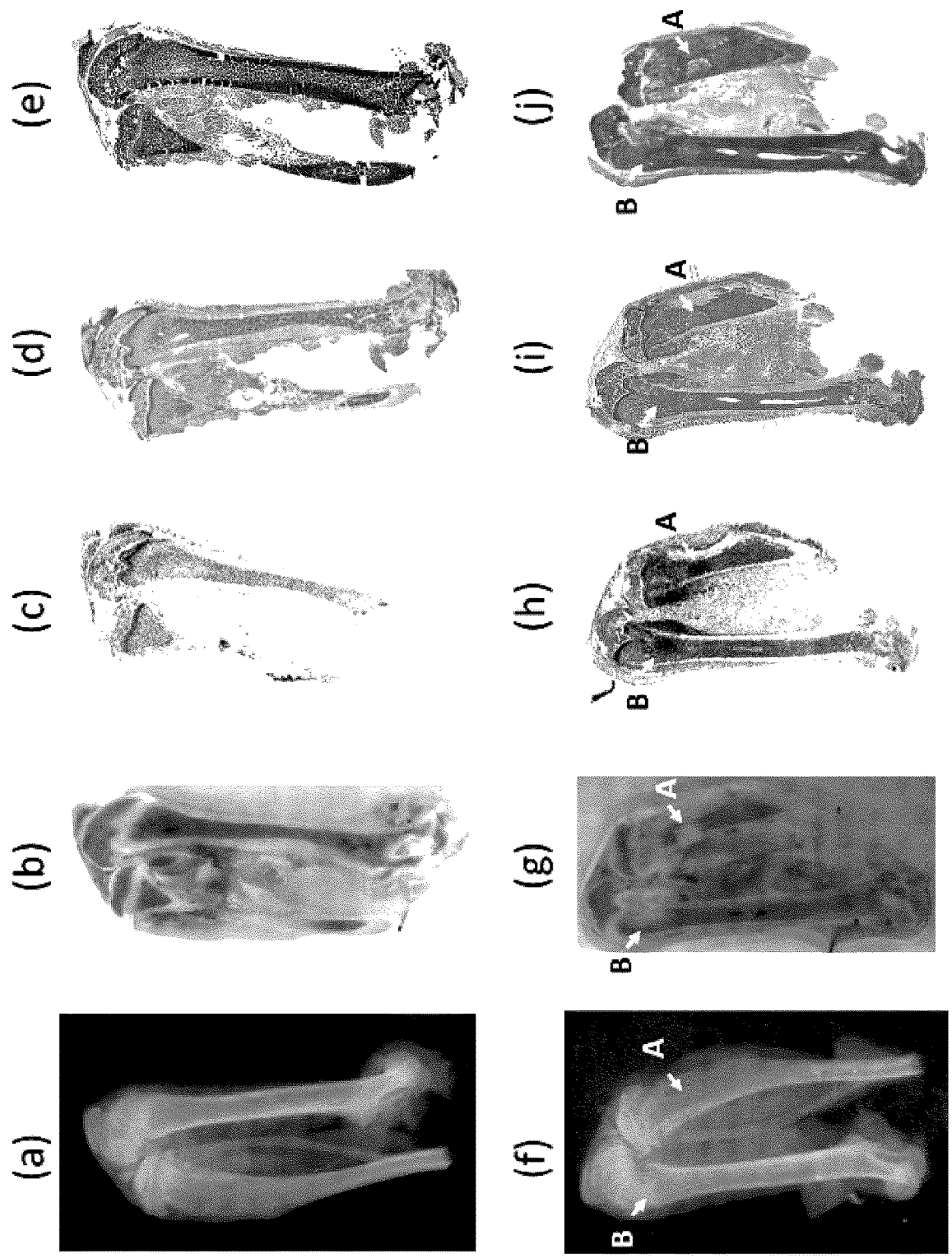

[Fig. 2]
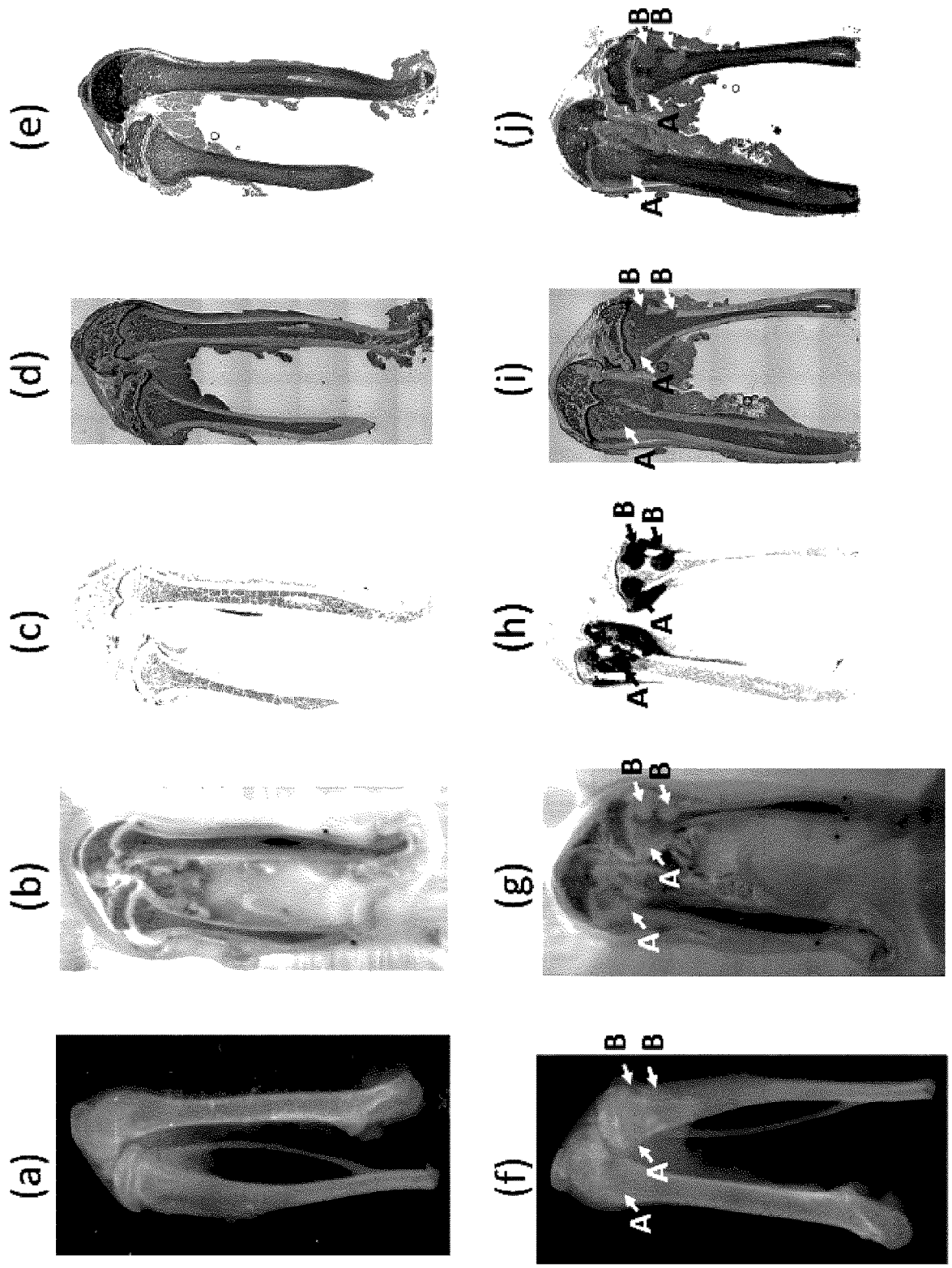

[Fig. 3]
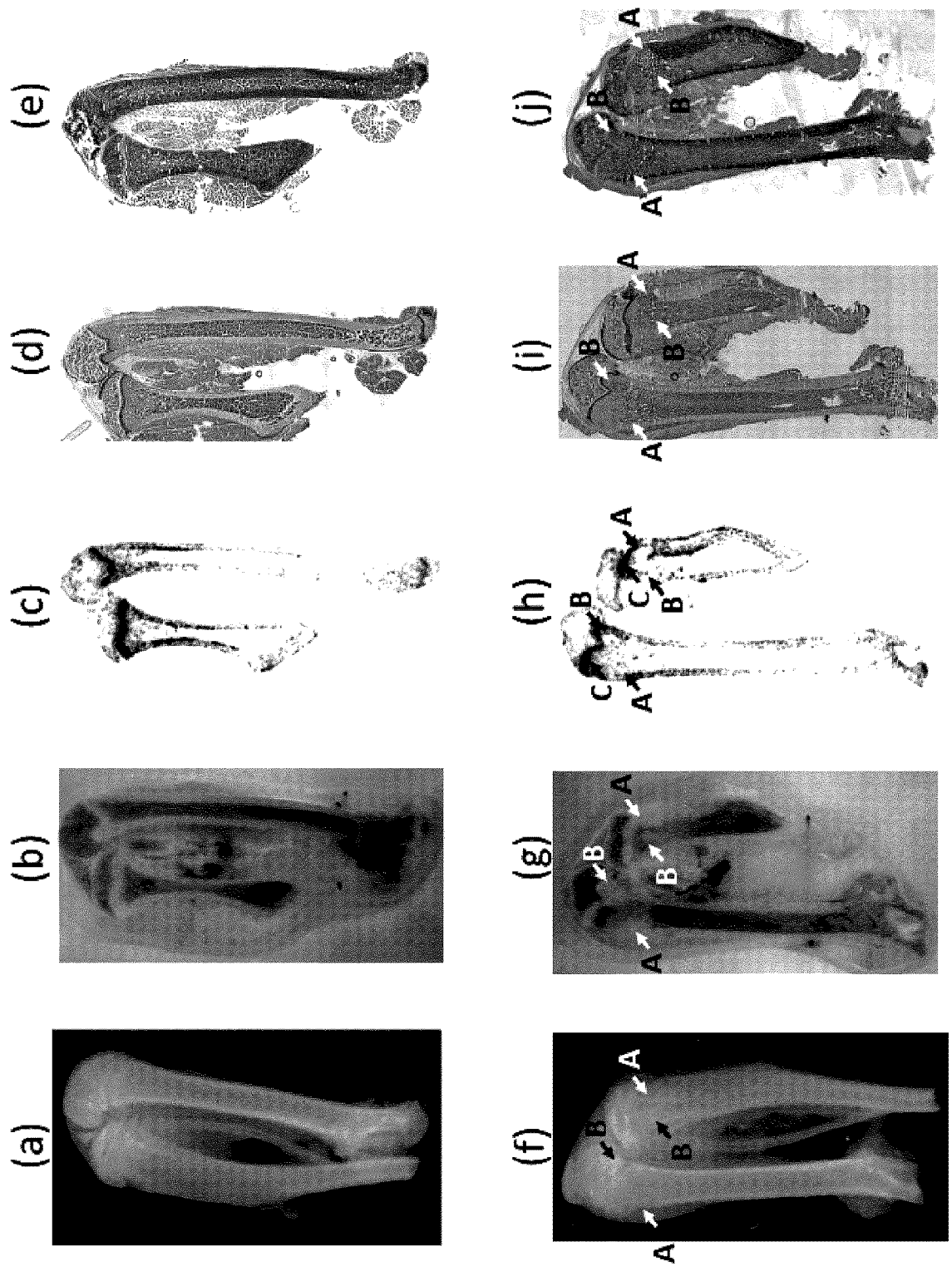

[Fig. 4]
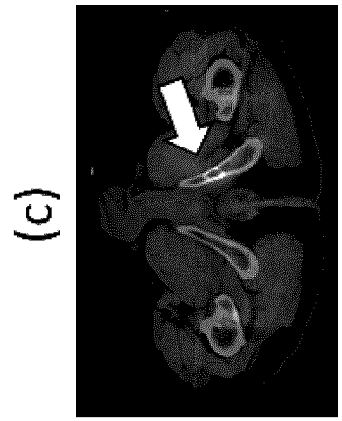
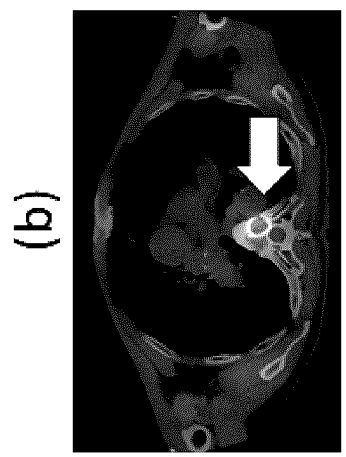
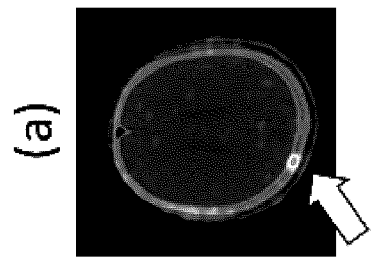

[Fig. 5]
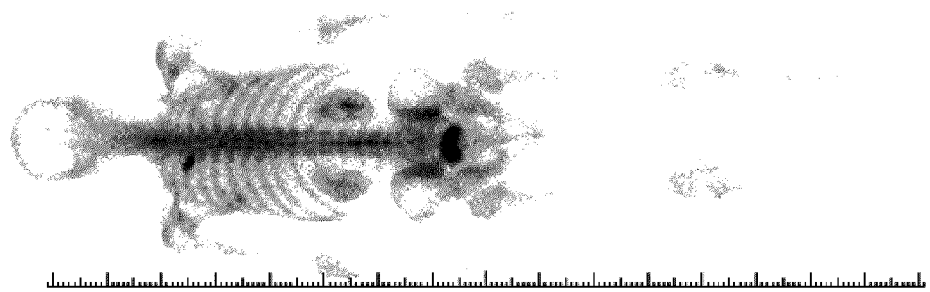
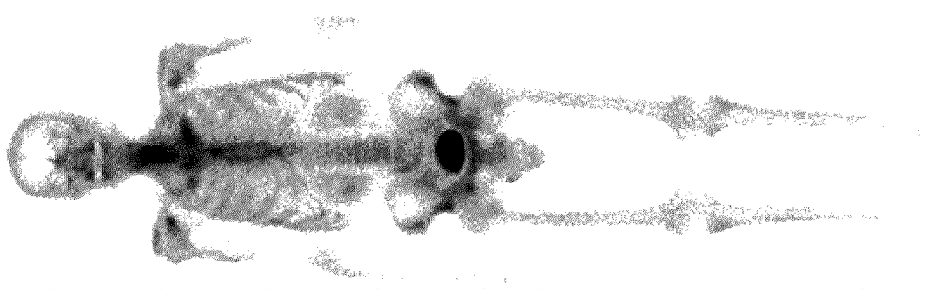
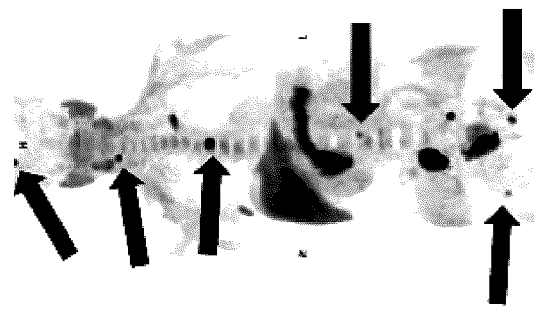

[Fig. 6]
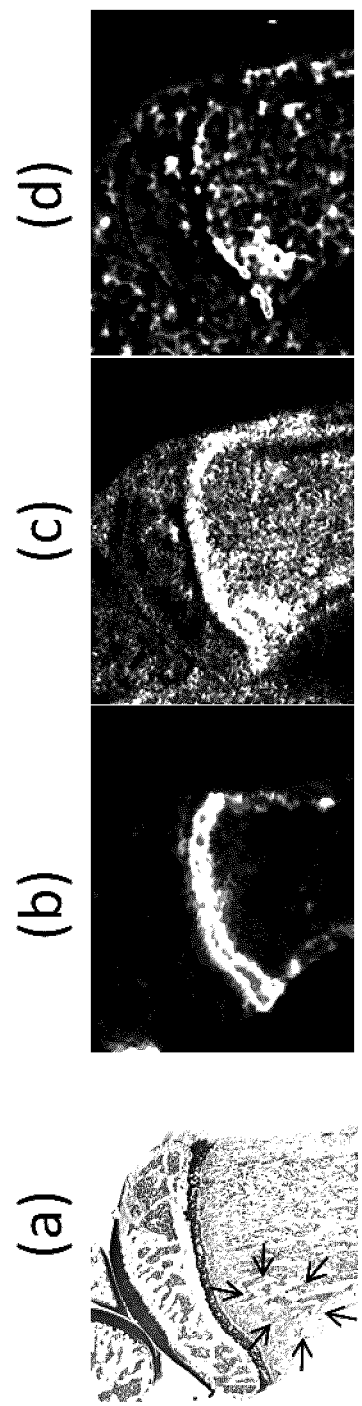

[Fig. 7]
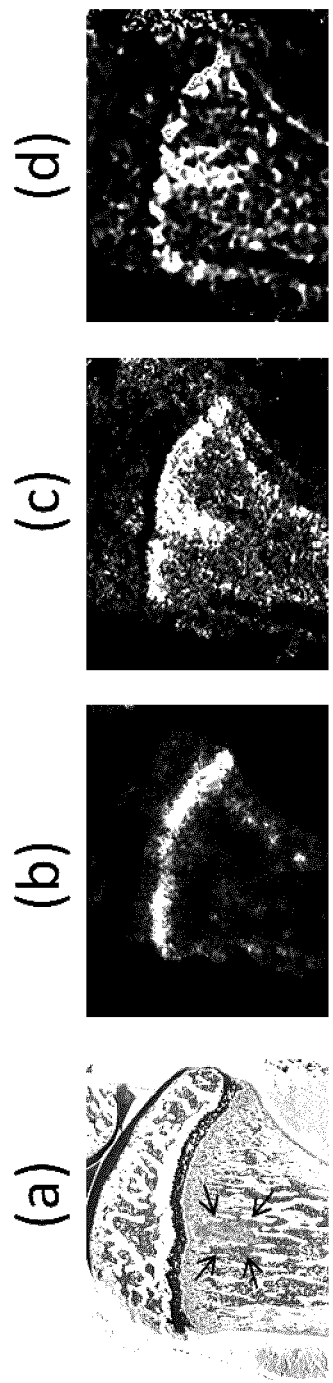

[Fig. 8]
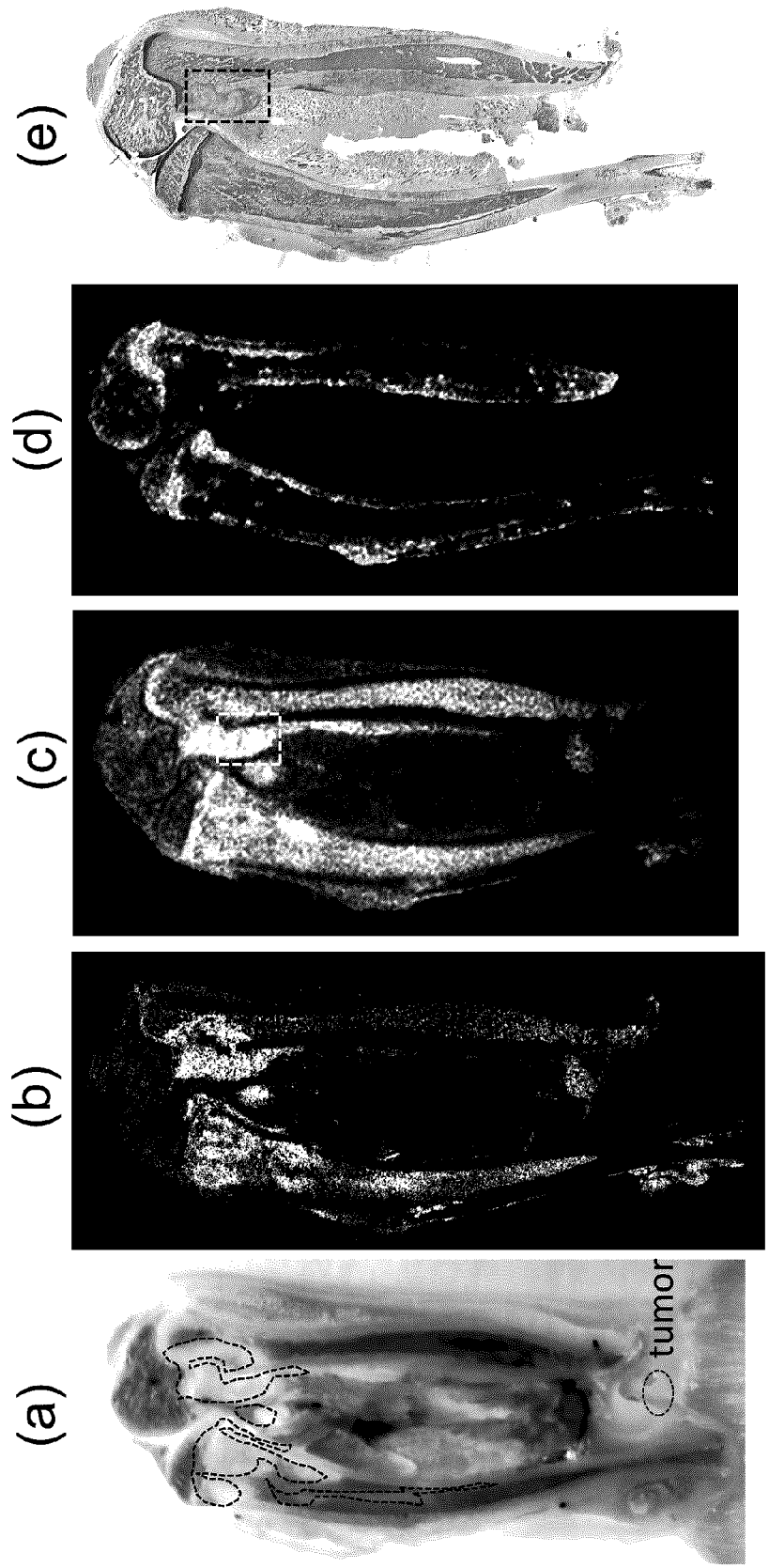

DIAGNOSTIC IMAGING AGENT FOR EARLY BONE METASTASIS FROM CANCER

TECHNICAL FIELD

The present invention relates to a diagnostic imaging agent for early bone metastasis from cancer.

BACKGROUND

As diagnostic imaging of bone metastasis, X-ray, computed tomography (CT), magnetic resonance imaging (MRI), bone scintigraphy by technetium[$^{99m}$Tc]hydroxymethylene diphosphonate ($^{99m}$Tc-HMDP) and technetium [$^{99m}$Tc]methylene diphosphonate ($^{99m}$Tc-MDP), and positron emission tomography (PET) by 2-[$^{18}$F]-2-deoxy-D-glucose ($^{18}$F-FDG) have been used. The morphological images of bone metastasis are obtained by X-ray, CT and MRI, and the functional images of bone metastasis are obtained by bone scintigraphy and PET. Therefore, these are also used in combination for the diagnosis of bone metastasis.

$^{18}$F-FDG reflects increased carbohydrate metabolism of cancer cells, and is therefore used as a diagnostic agent for not only bone metastasis but also various malignant tumors. On the other hand, $^{18}$F-FDG has problems as follows: (i) $^{18}$F-FDG also accumulates in normal tissues with high carbohydrate metabolism (such as brain and heart); (ii) since $^{18}$F-FDG is transferred to the bladder early after administration due to high urinary excretion, it is difficult to detect the clinical condition of the bladder and its periphery; and (iii) since $^{18}$F-FDG also accumulates in inflammatory tissues, it is difficult to distinguish tumors and inflammatory tissues. Therefore, various tumor diagnostic agents for PET that focus on an increase in metabolic ability of cancer cells different from carbohydrate metabolism have also been developed in recent years. As an agent to reflect the amino acid metabolism of cancer cells, for example, [$^{11}$C]methionine ($^{11}$C-methionine), trans-1-amino-[$^{18}$F]fluorocyclobutanecarboxylic acid ($^{18}$F-fluciclovine) and the like are known. Among these, $^{18}$F-fluciclovine has been developed as a diagnostic agent capable of visualizing prostate cancer which is difficult to visualize by $^{18}$F-FDG (Non-Patent Document 1-4).

CITATION LIST

Non Patent Literature

NPL 1: Shuster D. et al, J. Nucl. Med. (2007), vol. 48, No. 1, pp. 56-63
NPL 2: Shuster D. et al, Radiology (2011), vol. 259, No. 3, pp. 852-861
NPL 3: Oka S. et al, Mol. Imaging Biol. (2014), vol. 16, No. 3, pp. 322-329
NPL 4: Inoue Y. et al, Asia Oceania J. Nucl. Med. Biol. (2014), vol. 2, No. 2, pp. 87-94
NPL 5: Nakai T. et al., Eur J. Nucl. Med. Mol. Imaging (2005), vol. 32, No. 11, pp. 1253-1258

SUMMARY

In nuclear medicine diagnosis, even when different diagnostic agents are used for the same test, different information is presented depending on accumulation mechanism peculiar to each diagnostic agent. For example, $^{99m}$Tc-HMDP and $^{99m}$Tc-MDP reflect bone metabolism, whereas $^{18}$F-FDG reflects the increased carbohydrate metabolism of cancer cells as described above. Therefore, detectability can be different depending on the type of bone metastasis.

The image patterns of bone metastasis are generally classified into osteoblastic, osteolytic and mixed types. Bone scintigraphy has high sensitivity to osteoblastic bone metastasis, but osteolytic bone metastasis appears as a cold defect or does not show obvious changes thereon. Nakai T. et al., Eur J. Nucl. Med. Mol. Imaging (2005), vol. 32, No. 11, pp. 1253-1258 reports as follows: the combined "sensitivity" of all sites in 89 patients with breast cancer is "78.2%" for $^{99m}$Tc-HMDP and "80.0%" for $^{18}$F-FDG, and both agents do not have differences; however, when it comes to detection rates depending on the type of bone metastasis decided by CT, the detection rate of osteoblastic bone metastasis by $^{99m}$Tc-HMDP is higher than that by $^{18}$F-FDG (100%>55.6%), whereas the detection rate of osteolytic bone metastasis by $^{18}$F-FDG is higher than that by $^{99m}$Tc-HMDP (100%>70.0%).

In recent years, intertrabecular bone metastasis has been also proposed in which cancer cells histopathologically infiltrate and proliferate between trabeculae (bone marrow) but osteolytic and osteoblastic changes are not caused in trabeculae. It is difficult to capture metastasis prior to the onset of osteolytic response including the intertrabecular bone metastasis, and early bone metastasis of osteoblastic bone metastasis by bone scintigraphy and CT.

The intertrabecular bone metastasis can be detected using $^{18}$F-FDG; however, $^{18}$F-FDG is also incorporated into inflammatory cells developed by fractures and inflammatory responses, and there is therefore a possibility to show false positives.

The present invention has been made in view of the above-mentioned circumstances and provides a technique which can detect early bone metastasis from cancer with high accuracy.

According to an aspect of the present invention, there is provided a diagnostic imaging agent for early bone metastasis from cancer, containing trans-1-amino-[$^{18}$F]fluorocyclobutanecarboxylic acid ($^{18}$F-fluciclovine) or a pharmaceutically acceptable salt thereof as an active ingredient.

Further, according to another aspect of the present invention, there is provided a use of $^{18}$F-fluciclovine or a pharmaceutically acceptable salt thereof to produce a diagnostic imaging agent for early bone metastasis from cancer.

According to the present invention, bone metastasis of a type which is difficult to detect by existing diagnostic imaging such as bone scintigraphy and CT can be detected with high accuracy.

BRIEF DESCRIPTION OF DRAWINGS

FIGS. 1(a) to (j) are figures showing the evaluation results of $^{14}$C-fluciclovine using a rat model of osteolytic bone metastasis from breast cancer, (a) is a figure showing the result of X-ray imaging of lower limb bones removed from a normal limb (left hind limb), (b) is a figure showing the appearance of a section of lower limb bones removed from a normal limb (left hind limb), (c) is a figure showing the autoradiogram of lower limb bones removed from a normal limb (left hind limb), (d) is a figure showing the result of toluidine blue staining of lower limb bones removed from a normal limb (left hind limb), (e) is a figure showing the result of hematoxylin-eosin staining of lower limb bones removed from a normal limb (left hind limb), (f) is a figure showing the result of X-ray imaging of lower limb bones removed from a limb transplanted with MRMT-1 (right hind limb), (g) is a figure showing the appearance of a section of lower limb bones removed from a limb transplanted with MRMT-1 (right hind limb), (h) is a figure showing the autoradiogram of lower limb bones removed from a limb transplanted with MRMT-1 (right hind limb), (i) is a figure showing the result of toluidine blue staining of lower limb bones removed from a limb transplanted with MRMT-1 (right hind limb), and (j) is a figure showing the result of hematoxylin-eosin staining of lower limb bones removed from a limb transplanted with MRMT-1 (right hind limb).

FIGS. 2(a) to (j) are figures showing the evaluation results of $^3$H-FDG using a rat model of osteolytic bone metastasis from breast cancer, (a) is a figure showing the result of X-ray imaging of lower limb bones removed from a normal limb (left hind limb), (b) is a figure showing the appearance of a section of lower limb bones removed from a normal limb (left hind limb), (c) is a figure showing the autoradiogram of lower limb bones removed from a normal limb (left hind limb), (d) is a figure showing the result of toluidine blue staining of lower limb bones removed from a normal limb (left hind limb), (e) is a figure showing the result of hematoxylin-eosin staining of lower limb bones removed from a normal limb (left hind limb), (f) is a figure showing the result of X-ray imaging of lower limb bones removed from a limb transplanted with MRMT-1 (right hind limb), (g) is a figure showing the appearance of a section of lower limb bones removed from a limb transplanted with MRMT-1 (right hind limb), (h) is a figure showing the autoradiogram of lower limb bones removed from a limb transplanted with MRMT-1 (right hind limb), (i) is a figure showing the result of toluidine blue staining of lower limb bones removed from a limb transplanted with MRMT-1 (right hind limb), and (j) is a figure showing the result of hematoxylin-eosin staining of lower limb bones removed from a limb transplanted with MRMT-1 (right hind limb);

FIGS. 3(a) to 3(j) are figures showing the evaluation results of $^{99m}$Tc-HMDP using a rat model of osteolytic bone metastasis from breast cancer, (a) is a figure showing the result of X-ray imaging of lower limb bones removed from a normal limb (left hind limb), (b) is a figure showing the appearance of a section of lower limb bones removed from a normal limb (left hind limb), (c) is a figure showing the autoradiogram of lower limb bones removed from a normal limb (left hind limb), (d) is a figure showing the result of toluidine blue staining of lower limb bones removed from a normal limb (left hind limb), (e) is a figure showing the result of hematoxylin-eosin staining of lower limb bones removed from a normal limb (left hind limb), (f) is a figure showing the result of X-ray imaging of lower limb bones removed from a limb transplanted with MRMT-1 (right hind limb), (g) is a figure showing the appearance of a section of lower limb bones removed from a limb transplanted with MRMT-1 (right hind limb), (h) is a figure showing the autoradiogram of lower limb bones removed from a limb transplanted with MRMT-1 (right hind limb), (i) is a figure showing the result of toluidine blue staining of lower limb bones removed from a limb transplanted with MRMT-1 (right hind limb), and (j) is a figure showing the result of hematoxylin-eosin staining of lower limb bones removed from a limb transplanted with MRMT-1 (right hind limb);

FIGS. 4(a) to 4(c) are PET/CT images of a patient with prostate cancer using $^{18}$F-fluciclovine, (a) is a head image, (b) is a breast image, and (c) is a pelvic image; and FIGS. 5(a) to 5(c) are nuclear medicine images of a patient with prostate cancer, (a) is a $^{18}$F-fluciclovine PET image by the maximum intensity projection, (b) is an anterior image of bone scintigraphy, and (c) is a posterior image of bone scintigraphy.

FIGS. 6(a) to 6(d) are figures showing the evaluation results of triple tracer autoradiography (ARG) using a rat model of intertrabecular bone metastasis from breast cancer at day 6 after the transplantation of breast cancer cells, (a) is a figure showing the result of toluidine blue staining, (b) is a figure showing the autoradiogram of $^{99m}$Tc-HMDP, (c) is a figure showing the autoradiogram of $^{14}$C-fluciclovine, and (d) is a figure showing the autoradiogram of $^3$H-FDG.

FIGS. 7(a) to 7(d) are figures showing the evaluation results of triple tracer ARG using a rat model of intertrabecular bone metastasis from breast cancer at day 8 after the transplantation of breast cancer cells, (a) is a figure showing the result of toluidine blue staining, (b) is a figure showing the autoradiogram of $^{99m}$Tc-HMDP, (c) is a figure showing the autoradiogram of $^{14}$C-fluciclovine, and (d) is a figure showing the autoradiogram of $^3$H-FDG.

FIGS. 8(a) to 8(d) are figures showing the evaluation results of triple tracer ARG using a rat model of osteolytic bone metastasis from breast cancer at day 11 after the transplantation of breast cancer cells, (a) is a figure showing the appearance of a section of lower limb bones removed from a limb transplanted with MRMT-1, (b) is a figure showing the autoradiogram of $^3$H-FDG, (c) is a figure showing the autoradiogram of $^{14}$C-fluciclovine, (d) is a figure showing the autoradiogram of $^{99m}$Tc-HMDP, and (e) is a figure showing the result of toluidine blue staining.

DESCRIPTION OF THE EMBODIMENTS

In the present invention, "the diagnostic imaging agent" is used for positron emission tomography (PET), and specifically makes it possible to non-invasively diagnose clinical conditions by, after administration to a living organism, detecting and imaging radiation emitted from the body by PET equipment.

In the present invention, "bone metastasis" from cancer is a clinical condition in which a primary cancer developed in tissue other than bone metastasizes to bone. Examples of the "cancer developed in tissue other than bone" include breast cancer, kidney cancer, thyroid cancer, multiple myeloma, malignant lymphoma, prostate cancer, small cell lung cancer, liver cancer and pancreatic cancer. The targets of the diagnostic imaging agent of the present invention are preferably breast cancer and prostate cancer. Bone metastasis has osteolytic, osteoblastic and intertrabecular types and these types may be mixed, and bone metastasis is only required to predominate among all foci.

In the present invention, "early bone metastasis from cancer" means any of bone metastasis prior to the onset of osteolytic response, early osteoblastic bone metastasis, and intertrabecular bone metastasis. The "intertrabecular bone metastasis" means that although cancer cells histopathologically infiltrate and proliferate between trabeculae (bone marrow), any changes in bone do not occur.

The active ingredient of the diagnostic imaging agent of the present invention is $^{18}$F-fluciclovine or a pharmaceutically acceptable salt thereof.

$^{18}$F-fluciclovine can be synthesized by a known method, and for example can be obtained using a method described in Journal of Labelled Compounds and Radiopharmaceuticals, (1999), vol. 42, pp. 215-225.

In the present invention, as the "salt", pharmaceutically acceptable salts are not restricted. Examples thereof include salts derived from inorganic acids such as hydrochloric acid, hydrobromic acid, sulfuric acid, nitric acid and phosphoric acid; organic acids such as acetic acid, maleic acid, succinic acid, mandelic acid, fumaric acid, malonic acid, pyruvic acid, oxalic acid, glycolic acid, salicylic acid, pyranosidyl acid (glucuronic acid, galacturonic acid, etc.), α-hydroxy acid (citric acid, tartaric acid, etc.), amino acids (aspartic acid, glutamic acid, etc.), aromatic acids (benzoic acid, cinnamic acid, etc.) and sulfonic acid (p-toluenesulfonic acid, ethanesulfonic acid, etc.); organic bases such as amino acids (glycine, arginine, etc.), ammonia and primary, secondary and tertiary amines and cyclic amines (piperidine, morpholine, piperazine, etc.); or inorganic bases such as sodium hydroxide, calcium hydroxide, potassium hydroxide, magnesium hydroxide, manganese hydroxide, iron hydroxide, copper hydroxide, zinc hydroxide, aluminum hydroxide and lithium hydroxide.

The diagnostic imaging agent of the present invention is preferably administered by a parenteral means. Its dosage form is more preferably an injection, and preferably an aqueous solution, which can appropriately contain additional ingredients such as a pH regulator and a pharmaceutically acceptable solubilizer, tonicity agent, stabilizer and/or antioxidant.

The $^{18}$F-fluciclovine content of the diagnostic imaging agent of the present invention is not particularly restricted as long as the agent has the amount of radioactivity capable of PET imaging when used. As long as the agent has for example a radioactivity amount of 50 to 740 MBq when used, it is practical for PET imaging to adults.

EXAMPLES

The present invention will now be described in more detail by way of examples. It should be noted however that the present invention is not restricted to the contents thereof.

Example 1: Evaluation Using Rat Model of Osteolytic Bone Metastasis from Breast Cancer 1. Materials (1) Preparation of Breast Cancer Cell (MRMT-1) Suspension A rat breast cancer cell line MRMT-1 was obtained from RIKEN BioResource Center. MRMT-1 was subcultured using a medium RPMI1640 (manufactured by Life Technologies Japan Ltd.) with 10% fetal bovine serum (American Type Culture Collection), 100 U/mL penicillin (manufactured by Life Technologies Japan Ltd.), and 0.1 mg/mL streptomycin (manufactured by Life Technologies Japan Ltd). On the day of transplantation, the medium in a culture vessel was removed and Trypsin-EDTA solution (manufactured by Life Technologies Japan Ltd.) maintained at 37° C. was added to the culture vessel, which was left to stand at 37° C. for about 5 minutes. After MRMT-1 was detached from the surface of the culture vessel, the above-mentioned medium was added to the culture vessel in an amount equal to that of Trypsin-EDTA solution. MRMT-1 was precipitated by centrifugation (800 rpm, 5 min) and its supernatant was removed, and a cell suspension in which MRMT-1 was suspended in Hank's buffer (manufactured by Life Technologies Japan Ltd.) at a concentration of $2.5 \times 10^5$ cells/mL was then produced.

(2) Production of Rat Model of Osteolytic Bone Metastasis from Breast Cancer

An anti-inflammatory analgesic, Metacam 0.5% Solution for Injection (manufactured by Boehringer Ingelheim Vetmedica Japan Co., Ltd.) was subcutaneously injected into the groin of the right hind limb of 9-week-old male SD rat (Japan SLC, Inc.) at a rate of 0.2 mg/kg under isoflurane (manufactured by Mylan) anesthesia, and the skin in the groin was then incised. Next, the saphenous artery, the saphenous vein and the nerve parallel thereto were removed from muscles and isolated, and a surgical suture (3-0) was passed under the saphenous artery in the portion distal to the popliteal artery bifurcation. In addition, tissues around the superficial epigastric artery bifurcation were removed and a surgical suture (3-0) was passed under the femoral artery between the superficial epigastric artery bifurcation and the popliteal artery bifurcation (the portion slightly distal to the superficial epigastric artery bifurcation). Subsequently, a few drops of Papaverine Hydrochloride Injection 40 mg (manufactured by Nichi-Iko Pharmaceutical Co., Ltd.) was added dropwise around the saphenous artery to relax vascular smooth muscle, and each end of the surgical suture passed under the saphenous artery and the femoral artery was picked up with forceps, and the saphenous artery and the femoral artery were lifted to compress the arteries. A cotton swab was put under the saphenous artery to retain the saphenous artery, and an injection needle was inserted from the distal portion of the saphenous artery in the central direction, and MRMT-1 suspension (0.1 mL) was slowly injected. A drop of a surgical adhesive (Aron Alpha A "Sankyo" (registered trademark) manufactured by Toagosei Co., Ltd.) was added dropwise to the insertion site of the injection needle, and a subcutaneous fat piece taken from the operative field was put on the insertion site to close the site. The surgical suture was removed from the saphenous artery and femoral artery, and blood flow was restored. Subcutaneous fat around from the femoral artery to the abdominal aorta was repositioned, and the skin was closed with a surgical suture (5-0). Finally, an antibiotic, FOSMICIN-S 0.5 g FOR INJECTION (manufactured by Meiji Seika Pharma Co., Ltd.) was subcutaneously injected at a rate of 10 to 20 mg/kg. The produced model animal was used for the following experiment at day 12 to 14 after the transplantation.

(3) Preparation of trans-1-amino-3-fluorocyclobutane-1-[$^{14}$C]carboxylic acid ($^{14}$C-fluciclovine)

$^{14}$C-Fluciclovine was prepared in accordance with a method described in Nucl. Med. Biol. 39, 109-119.

2. Method

After photographing the rat model of osteolytic bone metastasis from breast cancer at day 12 after the transplantation of breast cancer cells with a microfocus X-ray imaging system (μFX-1000, manufactured by FUJIFILM Corporation), $^{14}$C-fluciclovine (1.05 MBq, 2.75 MBq/kg) was injected into the tail vein, and the rat model was sacrificed after 30 minutes. The right and left hind limbs were embedded in SCEM (manufactured by Section-lab Co. Ltd.) and then quickly frozen with isopentane/dry ice or hexane/dry ice, and sliced to a thickness of 10 m using a cryostat (manufactured by Leica Instruments GmbH). At this time, Cryofilm type IIC (9) (manufactured by Section-lab Co. Ltd.) was stuck on the sample surface and the sample was sliced to produce a bone section with a thickness of 10 m. The bone section was stuck on a slide glass (manufactured by Matsunami Glass Ind., Ltd.) with a double-stick tape with Cryofilm type IIC (9) down, and exposed on an imaging plate (manufactured by GE Healthcare Japan) for a week, and autoradiograms were analyzed using a scanner type image analyzer (Typhoon FLA 7000 IP system, manufactured by GE Healthcare Japan).

In addition, models to which $^3$H-FDG (manufactured by American Radiolabeled Chemicals) or $^{99m}$Tc-HMDP (manufactured by Nihon Medi-Physics Co., Ltd.) was administered in place of $^{14}$C-fluciclovine were prepared for comparison. When $^3$H-FDG was administered, the same operations were carried out except that the amount administered was 6.66 MBq (18.4 MBq/kg). When $^{99m}$Tc-HMDP was administered, the same operations were carried out except that the amount administered to the rat model of osteolytic bone metastasis from breast cancer at day 14 after the transplantation of breast cancer cells was 20.3 MBq (58.0 MBq/kg), the rat model was then sacrificed after 2 hours, and the exposure time to an imaging plate was 2 hours. As the type of imaging plate, TR was used for β nuclides, $^{14}$C-fluciclovine and $^3$H-FDG, and SR was used for γ nuclides, $^{99m}$Tc-HMDP.

After that, each section was pathologically evaluated by toluidine blue staining and hematoxylin-eosin staining. In the toluidine blue staining, a bone section with a thickness of 10 μm stuck on a slide glass was taken out from a cryostat and dried at room temperature for about a minute, and then soaked in Anhydrous Ethanol (manufactured by Wako Pure Chemical Industries, Ltd.) for about 3 to 5 seconds, and further soaked in 4% Paraformaldehyde Phosphate Buffer Solution (manufactured by Wako Pure Chemical Industries, Ltd.) for a minute or more. The section was washed with running water for about 10 seconds and then soaked in 0.05% Toluidine Blue Solution (pH 7.0) (manufactured by Wako Pure Chemical Industries, Ltd.) for about 5 minutes. The section was washed with running water for about 30 seconds, and a few drops of a dedicated mounting medium, SCMM-R3 (manufactured by Section-lab Co. Ltd.) was then added dropwise to the surface of the bone section, and both edges of Cryofilm type IIC (9) were cut out with a cutter. The sample was put on another slide glass with the bone section down, and the dedicated mounting medium was polymerized by a polymerizer for the dedicated mounting media (R2•R3) (manufactured by Leica Microsystems).

In the hematoxylin-eosin staining, the bone section was soaked in Anhydrous Ethanol and 4% Paraformaldehyde Phosphate Buffer Solution in the same manner as above and then soaked in Haematoxylin 3G (manufactured by Sakura Finetek Japan Co., Ltd.) for about 2 minutes, and washed with running water for about 30 seconds. Next, the section was soaked in Eosin (manufactured by Sakura Finetek Japan Co., Ltd.) for about a minute and then washed with running water for about 30 seconds. A few drops of a dedicated mounting medium, SCMM-R2 (manufactured by Section-lab Co. Ltd.) was added dropwise to the surface of the bone section and the dedicated mounting medium was then polymerized in the same manner as in toluidine blue staining.

3. Results

The results are shown in FIGS. 1-3. FIGS. 1(a) to (j) are figures showing the results of $^{14}$C-fluciclovine, FIGS. 2(a) to (j) are figures showing the results of $^3$H-FDG, and FIGS. 3(a) to (j) are figures showing the results of $^{99m}$Tc-HMDP. FIGS. 1(a) to (e), FIGS. 2(a) to (e), and FIGS. 3(a) to (e) show lower limb bones removed from a normal limb (left hind limb), and FIGS. 1(f) to (j), FIGS. 2(f) to (j), and FIGS. 3(f) to (j) show lower limb bones removed from a limb transplanted with MRMT-1 (right hind limb). FIGS. 1(a) and (f), FIGS. 2(a) and (f), and FIGS. 3(a) and (f) are the results of X-ray imaging, FIGS. 1(b) and (g), FIGS. 2(b) and (g), and FIGS. 3(b) and (g) are the visual appearance of the section, FIGS. 1(c) and (h), FIGS. 2(c) and (h), FIGS. 3(c) and (h) are autoradiograms, FIGS. 1(d) and (i), FIGS. 2(d) and (i), and FIGS. 3(d) and (i) are the results of toluidine blue staining, and FIGS. 1(e) and (j), FIGS. 2(e) and (j), and FIGS. 3(e) and 3(j) are the results of hematoxylin-eosin staining.

The arrow A in FIG. 1(f) shows an osteolytic lesion site observed in the X-ray image of a limb transplanted with MRMT-1 (right hind limb). The arrow A in FIG. 1(g) shows a focal site of bone metastasis observed in the visual appearance of the section of the limb transplanted with MRMT-1 (right hind limb), which is the same site as the arrow A in FIG. 1(f). The arrow A in FIG. 1(h) shows a site at which the accumulation of $^{14}$C-fluciclovine is observed in the autoradiogram of the limb transplanted with MRMT-1 (right hind limb), which is the same site as the arrow A in FIG. 1(f). The arrow A in FIG. 1(i) shows a focal site of bone metastasis observed in the toluidine blue staining image of the limb transplanted with MRMT-1 (right hind limb), which is the same site as the arrow A in FIG. 1(f). The arrow A in FIG. 1(j) shows a focal site of bone metastasis observed in the hematoxylin-eosin staining image of the limb transplanted with MRMT-1 (right hind limb), which is the same site as the arrow A in FIG. 1(f). These results confirmed that $^{14}$C-fluciclovine accumulated in bone metastasis in the osteolytic lesion area.

The arrow B in FIG. 1(f) shows a site at which an osteolytic lesion is not observed in the X-ray image of the limb transplanted with MRMT-1 (right hind limb). The arrow B in FIG. 1(g) shows a focal site of bone metastasis observed in the visual appearance of the section of the limb transplanted with MRMT-1 (right hind limb), which is the same site as the arrow B in FIG. 1(f). The arrow B in FIG. 1(h) shows a site at which the accumulation of $^{14}$C-fluciclovine is observed in the autoradiogram of the limb transplanted with MRMT-1 (right hind limb), which is the same site as the arrow B in FIG. 1(f). The arrow B in FIG. 1(i) shows a focal site of bone metastasis observed in the toluidine blue staining image of the limb transplanted with MRMT-1 (right hind limb), which is the same site as the arrow B in FIG. 1(f). The arrow B in FIG. 1(j) shows a focal site of bone metastasis observed in the hematoxylin-eosin staining image of the limb transplanted with MRMT-1 (right hind limb), which is the same site as the arrow B in FIG. 1(f). These results confirmed that $^{14}$C-fluciclovine also accumulated in bone metastasis prior to the formation of osteolytic lesion which cannot be detected in an X-ray image. The results confirmed that $^3$H-FDG also accumulated in the osteolytic lesion areas and bone metastasis prior to the formation of osteolytic lesion as shown by the arrows A and the arrows B in FIGS. 2(f) to (j). The above results confirmed that $^{14}$C-fluciclovine accumulated in the osteolytic lesion area and bone metastasis prior to the formation of osteolytic lesion as is the case with $^3$H-FDG. In the meantime, the accumulation of $^{99m}$Tc-HMDP was observed in the growth plate and around the primary cancellous bone (arrow C), but was observed in neither the osteolytic lesion areas (arrow A) nor the foci of bone metastasis prior to the formation of osteolytic lesion (arrow B).

Example 2: PET Imaging of Patient with Prostate Cancer

The test was carried out in accordance with the ethical principles based on the Declaration of Helsinki and GCP.

Prior to the test, the agreement in writing on voluntary test participation was obtained at first hand.

1. Patient

An untreated male patient (69-year-old man) histopathologically diagnosed with prostate cancer by prostate needle biopsy was selected, who had a PSA of 589.17 ng/mL and a Gleason score of 8.

2. Test Drug $^{18}$F-fluciclovine preparation (NMK36, manufactured by Nihon Medi-Physics Co., Ltd.) produced by a method described in WO2008/75522 was used.

3. PET/CT

The patient fasted after the evening meal of the previous day, and 2 mL of $^{18}$F-fluciclovine preparation (263.1 MBq) was intravenously administered and a saline was flushed. The $^{18}$F-fluciclovine preparation was administered after day 22 from the day of prostate needle biopsy (day 1) to avoid the action of the primary focus of prostate cancer on the evaluation of PET/CT images. A whole body CT image was taken immediately after the administration of the $^{18}$F-fluciclovine preparation using a PET/CT camera (Discovery PET/CT600 manufactured by GE Healthcare) for the purpose of attenuation correction and then a whole body PET was finished by 30 minutes after the administration.

4. Existing Images

For comparison with the $^{18}$F-fluciclovine PET/CT images, whole body contrast enhanced CT and bone scintigraphy were taken by 28 days prior to the day of $^{18}$F-fluciclovine PET/CT. For the whole body contrast enhanced CT, a non-ionic contrast agent (BYSTAGE, manufactured by FUJIFILM Medical Co., Ltd.) was administered, and after 90 seconds, CT imaging was initiated at a slice thickness of 5 mm or less using an 80-row multidetector CT (Aquilion Prime manufactured by TOSHIBA CORPORATION) from the neck to the pelvis (tube voltage: 120 kV). For the bone scintigraphy, 740 MBq $^{99m}$Tc-HMDP (CLEAR BONE (registered trademark) Injection, manufactured by Nihon Medi-Physics Co., Ltd.) was administered, and whole body planar images were initiated after two hours (energy window: 140 keV±10%).

5. Visual Image Evaluation

Two members to judge images, who were blinded to the subject background, each independently evaluated the $^{18}$F-fluciclovine PET/CT, whole body contrast enhanced CT and bone scintigraphy images. When two members had different decisions, a decision was made by discussion. The whole body planar images and whole body contrast enhanced CT images of bone scintigraphy were interpreted, and from the overall findings thereof, the presence or absence of bone metastasis was decided.

6. Results

The results are shown in FIGS. 4(a) to (c) and 5(a) to (c). FIGS. 4(a) to (c) are $^{18}$F-fluciclovine PET/CT images, FIG. 4(a) is a head image, FIG. 4(b) is a breast image, and FIG. 4(c) is a pelvic image. In addition, FIG. 5(a) is a $^{18}$F-fluciclovine PET image by the maximum intensity projection, FIG. 5(b) is an anterior image of bone scintigraphy, and FIG. 5(c) is a posterior image of bone scintigraphy. In FIGS. 4(a) to 4(c) and 5(a) to (c), the sites shown with the arrows were sites which were not visualized on bone scintigraphy in FIGS. 5(b) and (c) and further were not visualized on the whole body contrast enhanced CT. Thus, the lesions which were not visualized on bone scintigraphy and whole body contrast enhanced CT were visualized on the $^{18}$F-fluciclovine images.

Example 3: Triple Tracer Autoradiography

1. Material (1) Preparation of Breast Cancer Cell (MRMT-1) Suspension

MRMT-1 suspension was prepared in the same way as the MRMT-1 suspension prepared in Example 1.

(2) Production of Rat Model of Bone Metastasis from Breast Cancer

A model of intertrabecular bone metastasis was prepared in the same way as the rat model of osteolytic bone metastasis prepared in Example 1 except that a MRMT-1 suspension was injected into right and left saphenous arteries of the 12-week old male SD rat (Japan SLC, Inc.), which was used for the following experiment at day 6 or day 8 after the transplantation. The lesion appeared only in right hind limb of the model at day 6 after the transplantation and left limb of the model at day 8 after the transplantation.

A model of osteolytic bone metastasis was prepared in the same way as the rat model of osteolytic bone metastasis prepared in Example 1 except that the model was produced from 12-week old male SD rat (Japan SLC, Inc.), and used for the following experiment at day 11 after the transplantation.

(3) Preparation of $^{14}$C-Fluciclovine $^{14}$C-fluciclovine was prepared in the similar way as $^{14}$C-fluciclovine prepared in the Example 1.

2. Method

The rat models of intertrabecular bone metastasis from breast cancer at day 6 or 8 after the transplantation of breast cancer cells or the rat models of osteolytic bone metastasis from breast cancer at day 11 after the transplantation of breast cancer cells were fasted overnight and anesthetized with 1% isoflurane (manufactured by Pfizer Inc.) before administration of the tracers; 2.75 MBq/kg of $^{14}$C-fluciclovine, 74 MBq/kg of $^{99m}$Tc-HMDP (manufactured by Nihon Medi-Physics Co., Ltd.) and 18.5 MBq/kg of $^{3}$H-FDG (manufactured by American Radiolabeled Chemicals) were injected into the trail vein of an identical rat. $^{14}$C-fluciclovine and $^{3}$H-FDG were allowed to remain into circulation for 30 minutes and $^{99m}$Tc-HMDP for 2 hours prior to sacrifice. The animals were sacrificed under anesthesia by drawing blood from the abdominal aorta. Then, tibiae and femora were removed, embedded in SCEM (manufactured by Section-Lab Co. Ltd.) and frozen in isopentane/dry ice. The frozen samples were sectioned (5 μm- and 10 μm-thick slices for pathological and autoradiography specimens, respectively) with a CM3050S cryostat (manufactured by Leica Biosystems) at −20° C. as described in Kawamoto's film methods (Kawamoto T. Arch. Histol. Cytol. 2003; 66:123-43). Fifteen serial sections were obtained and each section was mounted on a glass slide. To obtain images generated by $^{99m}$Tc isotope, SR-imaging plates (manufactured by FUJIFILM Corporation) were exposed for 1 hour to dried 10 μm-thick slices wrapped in a 12-μm-thick polyester film (LUMIRROR™ manufactured by Toray Industries, Inc.), which absorbs low-energy $^3$H. Under these conditions, $^{14}$C caused no blackening of the SR-imaging plates even after a 1 hour exposure, thus excluding cross-contamination by $^{14}$C of the $^{99m}$Tc autoradiographs. The next 2 frozen sections adjacent to the $^{99m}$Tc-autoradiographed section were stored at −20° C. for 5 days to allow complete $^{99m}$Tc decay. Following this, TR-imaging plates (manufactured by FUJIFILM Corporation) were exposed to the dried sections with and without the 12 m-thick polyester film for 7 days to obtain $^{14}$C images and $^3$H+$^{14}$C mixed images, respectively (Obata T. et al. RADIOISOTOPES. 2000; 49:623-36). The imaging plates were developed with a FLA-7000 imaging analyzer (manufactured by GE Healthcare UK Ltd). Finally, $^3$H images were generated by subtracting $^{14}$C images from $^{14}$C+$^3$H images by using ImageJ software (ver. 1.48; NIH). All images were processed by using the ImageJ software and region-of-interest (ROI) analysis was performed as mentioned below. A five m-thick bone section was pathologically evaluated by toluidine blue in the same way as described in Example 1.

3. Results

The results of the model of intertrabecular bone metastasis are shown in FIGS. 6 and 7. FIG. 6 shows the result at day 6 after the transplantation of the breast cancer cell, and FIG. 7 shows the result at day 8 after the transplantation of the breast cancer cell. FIG. 6(a) and FIG. 7(a) are the results of toluidine blue staining, in which the arrows show a focal site of intertrabecular bone metastasis. The focal site of intertrabecular bone metastasis at day 6 after the transplantation of the breast cancer cell is of the intertrabecular type prior to formation of osteolytic lesion, and the focal site of intertrabecular bone metastasis at day 8 after the transplantation of the breast cancer cell is of the intertrabecular type mixed with the osteolytic type. FIG. 6(b) and FIG. 7(b) are figures showing the results of $^{99m}$Tc-HMDP, FIG. 6(c) and FIG. 7(c) are figures showing the results of $^{14}$C-fluciclovine, and FIG. 6(d) and FIG. 7(d) are figures showing the results of $^3$H-FDG.

Also, the results of the model of osteolytic bone metastasis are shown in FIG. 8. FIG. 8(a) is a figure showing the visual appearance of the prepared bone section, FIG. 8(b) is the result of $^3$H-FDG, FIG. 8(c) is the result of $^{14}$C-fluciclovine, FIG. 8(d) is the result of $^{99m}$Tc-HMDP, and FIG. 8(e) is the result of toluidine blue staining.

As shown in FIG. 6(c), FIG. 7(c) and FIG. 8(c), it was confirmed that $^{14}$C-fluciclovine accumulated in the early focal site of bone metastasis. Also, as shown in FIG. 6(d), FIG. 7(d) and FIG. 8(b), it was also confirmed that $^3$H-FDG accumulated in the early focal site of bone metastasis. However, as shown in FIG. 6(b), FIG. 7(b) and FIG. 8(d), no accumulation of $^{99m}$Tc-HMDP was observed in the early focal site of bone metastasis.

The above results suggested that early bone metastasis from cancer was able to be detected by $^{18}$F-fluciclovine.

This application claims the priority based on Japanese patent application No. 2015-113587 filed on Jun. 4, 2015 in the Japan Patent Office and the whole disclosure thereof is incorporated herein.

The invention claimed is:

1. A method of diagnosing early bone metastasis from cancer comprising administering trans-1-amino-[$^{18}$F]fluorocyclobutanecarboxylic acid or a pharmaceutically acceptable salt thereof to a living organism, and detecting and imaging radiation emitted from the organism, wherein the early bone metastasis from cancer is not detectable by bone scintigraphy, said early bone metastasis being one selected from the group consisting of bone metastasis prior to the onset of osteolytic response, early osteoblastic bone metastasis, and intertrabecular bone metastasis.

2. The method according to claim 1, wherein the trans-1-amino-[$^{18}$F]fluorocyclobutanecarboxylic acid or a pharmaceutically acceptable salt thereof is administered parenterally.

3. The method according to claim 1, wherein the imaging is by positron imaging tomography.

4. The method according to claim 1, wherein the organism has previously been diagnosed with prostate cancer.

5. The method according to claim 1, wherein the early bone metastasis is one selected from the group consisting of bone metastasis prior to the onset of osteolytic response, and early osteoblastic bone metastasis.

6. The method according to claim 1, wherein the early bone metastasis is bone metastasis prior to the onset of osteolytic response.

7. The method according to claim 1, wherein the early bone metastasis from cancer is bone metastasis accompanied with breast cancer or prostate cancer.

* * * * *